United States Patent [19]

Fujitsuka et al.

[11] Patent Number: 4,899,744
[45] Date of Patent: Feb. 13, 1990

[54] APPARATUS FOR ANASTOMOSING DIGESTIVE TRACT

[76] Inventors: Tatsuo Fujitsuka, 2061, Oaza Shinbori, Shobu-cho, Minamisaitama-gun, Saitama; Hiroshi Kawasaki, 17-9 Akabane 2-chome, Kita-ku, Tokyo, both of Japan

[21] Appl. No.: 284,618
[22] Filed: Dec. 15, 1988
[51] Int. Cl.$^4$ ............... A61B 17/04; A61B 17/11
[52] U.S. Cl. ............................ 606/153; 606/216
[58] Field of Search .............. 128/334 R, 334 C, 335

[56] References Cited

U.S. PATENT DOCUMENTS

| | | | |
|---|---|---|---|
| 3,974,835 | 8/1976 | Hardy, Jr. | 128/334 C |
| 4,055,186 | 10/1977 | Leveen | 128/334 C |
| 4,552,148 | 12/1985 | Hardy, Jr. | 128/334 C |
| 4,705,039 | 11/1987 | Sakaguchi et al. | 128/334 C |
| 4,708,141 | 11/1987 | Inoue et al. | 128/334 R |

FOREIGN PATENT DOCUMENTS

| | | | |
|---|---|---|---|
| 119848 | 3/1984 | European Pat. Off. | 128/334 C |
| 0218128 | 4/1987 | European Pat. Off. | 128/334 R |

Primary Examiner—Edward M. Coven
Assistant Examiner—Gary Jackson
Attorney, Agent, or Firm—James E. Nilles; Donald C. McGaughey

[57] ABSTRACT

An apparatus for anastomosing a digestive tract including a plurality of substantially U-shaped retainers that are disposed around an annular groove in the outer periphery of a support tube formed of a soluble material. The annular groove has inner side and bottom surfaces and the retainers are disposed in the tube at a plurality of locations along both the inner side surfaces and the inner bottom surface of the groove in a radial array. The retainers have spaced apart ends and are each made of a shape memory alloy or resin endowed with a property of moving the spaced apart ends to a closed state at a predetermined temperature, or made using a spring member, or provided at the spaced apart ends with magnets that will attract each other. In use, the retainers are released from the support tube when the soluble material of the support tube is dissolved and assume closed state when they reach the predetermined temperatures to clamp the digestive tract therebetween.

10 Claims, 7 Drawing Sheets

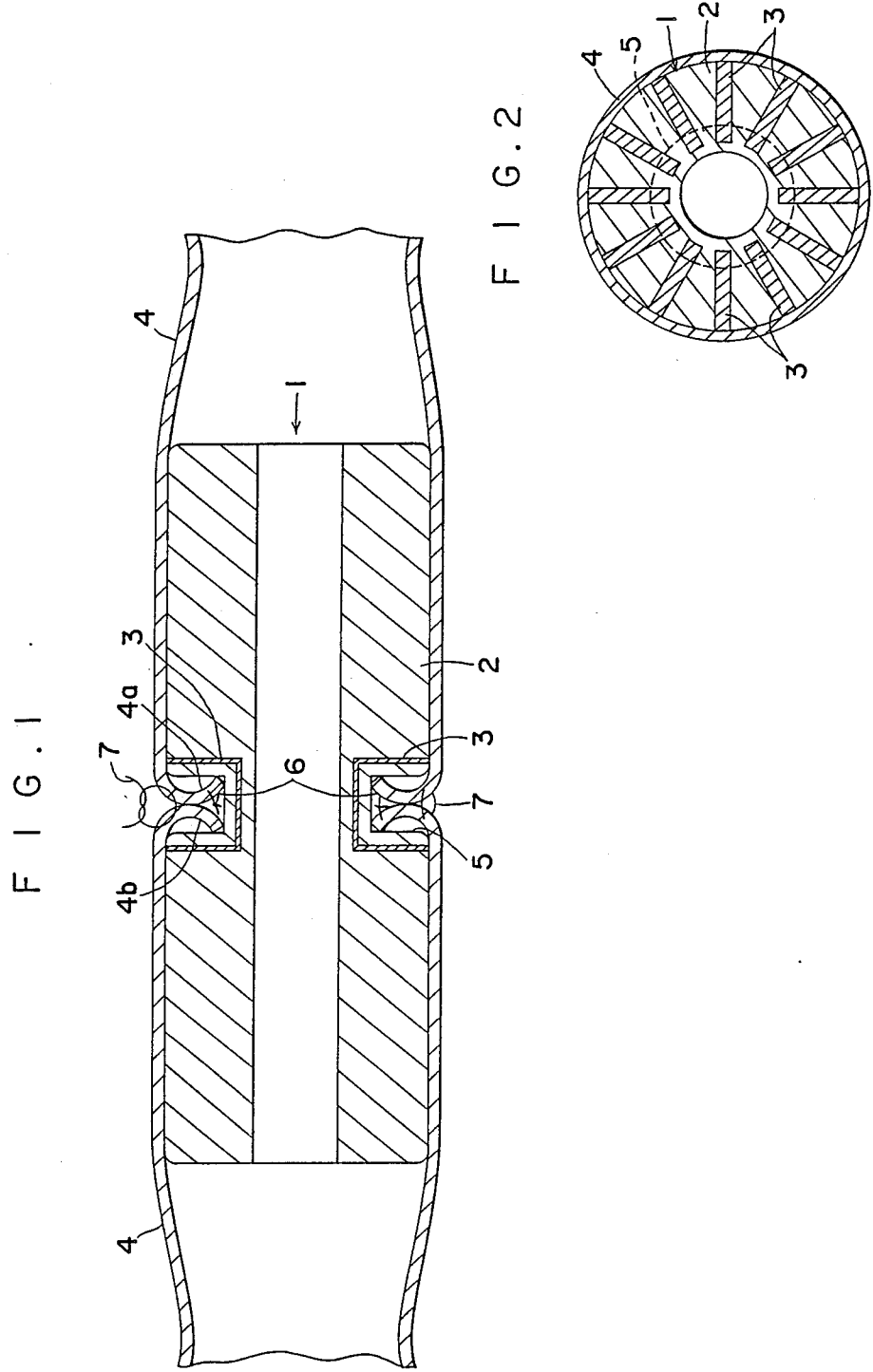

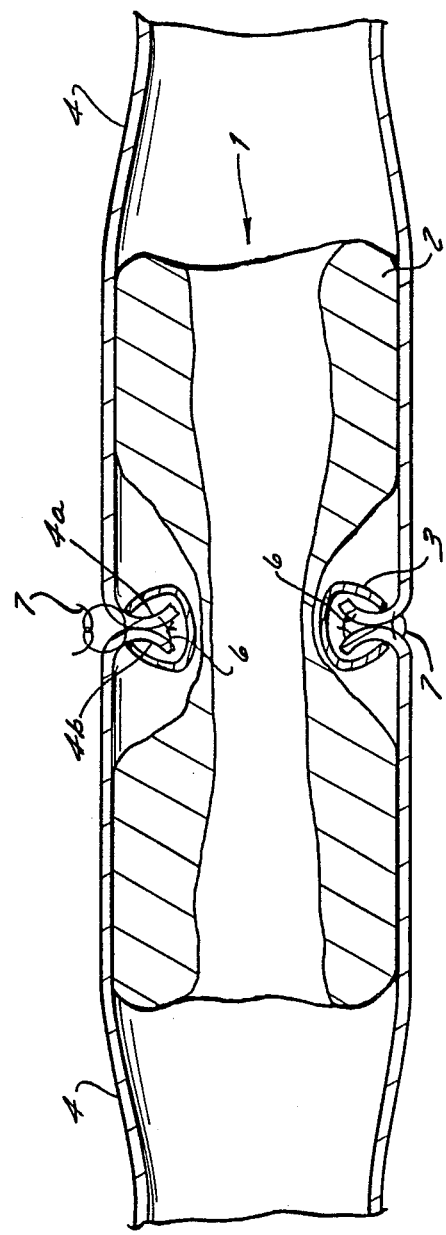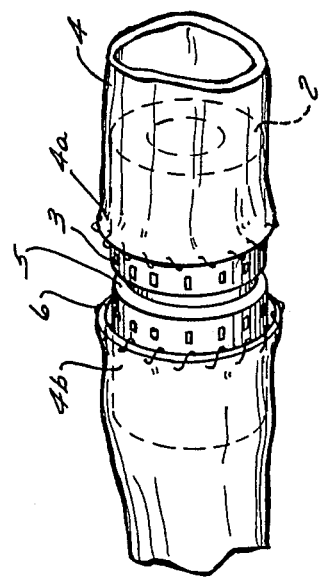
FIG. 3b
FIG. 3a

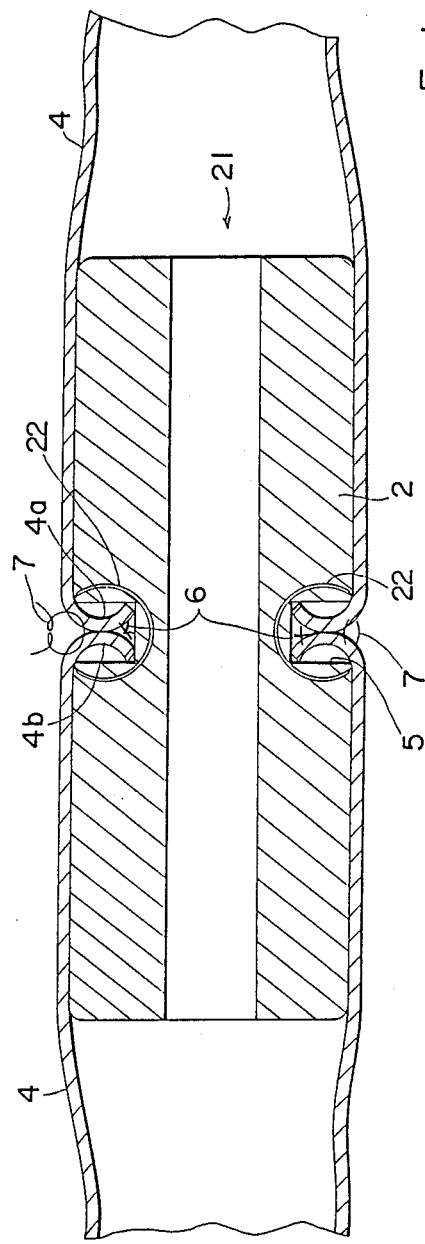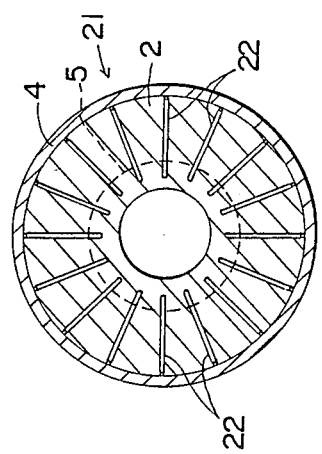

APPARATUS FOR ANASTOMOSING DIGESTIVE TRACT

BACKGROUND OF THE INVENTION

1. Field of the Invention

The present invention relates to an apparatus for anastomosing cut ends of a digestive tract extending from the esophagus to the rectum or the anus thereabout.

2. Description of the Prior Art

One of known apparatuses for anastomosing cut ends of a severed digestive tract during a surgical operation of the digestive tract is disclosed in Japanese Utility Model Publication No. 46-16477.

The disclosed apparatus includes a pair of ring-like joining members supported on a pipe and brought into pressure contact with each other by a spring or magnetic force, with both cut ends to be anastomosed being held between the pair of joining members. After adhesion of the cut ends, the members are removed through the esophagus or excreted through the rectum.

The foregoing conventional apparatus is effective when used in the esophagus or the rectum from which it can easily be removed or excreted. When it is used in the remaining portions, there arises a problem because a relatively large-sized solid foreign matter, which is the same size as when it was installed, must be removed or excreted. Another problem is that the conventional apparatus can be applied to end-to-end anastomosis as shown in FIG. 15 and end-to-side anastomosis as shown in FIG. 16, but it is not applicable to side-to-side anastomosis as shown in FIG. 17.

SUMMARY OF THE INVENTION

The present invention has been accomplished in view of the foregoing status in the art. It is an object of the present invention to provide an apparatus for anastomosing a digestive tract which requires the excretion of only small-sized foreign matters after adhesion of cut ends, thereby ensuring safety and lessening a burden imposed on patients.

The apparatus for anastomosing a digestive tract of the present invention includes a support tube formed of mainly a soluble material, an annular groove is defined in the outer periphery of the support tube, and a plurality of retainers each having spaced apart ends providing an open space therebetween when said retainer is in an open state endowed with a property of closing its spaced apart ends to a closed state, said retainers embedded around the groove in the support tube at a plurality of locations along both the inner side surfaces and the inner bottom surface of the groove in a radially arrayed pattern, the retainers being movable to the closed state wherein the digestive tract is clamped therebetween during use and then released from the support tube in their closed state as the soluble material of the support tube is dissolved.

The soluble material of the support tube can be formed of saccharides. The retainers can be each formed in a substantially U-shaped or arcuate with said spaced apart ends thereof opened when they are embedded in the support tube. The retainers can be formed to have their spaced apart ends opposite or overlapped with each other when said ends are closed, or made of a shape memory alloy or resin endowed with a property of closing its spaced apart ends at a predetermined temperature when used, or made using a spring member, or provided at its open opposite ends with magnets that attract the spaced apart ends to each other.

When using the apparatus of the present invention, opposite ends of the support tube are inserted into cut ends of a digestive tract to be anastomosed, respectively, and the cut ends are both engaged in the groove of the support tube. The spaced apart ends of each of a plurality of retainers are closed to hold, by clamping or squeezing, the cut ends of the digestive tract in the same manner as the inner suture of the standard two-layer inversion anastomosis. After this closed state is achieved, the soluble material of the support tube dissolves. Being left in that state, the cut ends of the digestive tract adhere to each other outside the plurality of retainers. When the parts of the anastomosed digestive tract held by the retainers inside the adhered portion are necrotized, the retainers fall off inside the digestive tract.

With the apparatus of the present invention, where saccharides are used as the soluble material of the support tube, human bodies are less affected. Further, where the retainers are each made of a shape memory alloy or resin, the force of closing the open opposite ends of each retainer can be sustained until the time of use, even when there is a prolonged storage period prior to use. Further, the retainers can be easily buried in the support tube. Where the retainers comprise spring members, they can be manufactured less expensively. Where the retainers are each provided at their spaced apart ends with magnets that attract each other, the held portions of the cut ends of the digestive tract are brought into surface-to-surface pressure contact. Where the retainers are each formed in a circle when in a closed state, the retainers becomes suitable for mass production.

Other objects and features of the present invention will be described with reference to the drawings.

BRIEF DESCRIPTION OF THE DRAWINGS

FIGS. 1 and 2 are a longitudinal sectional view and a transverse sectional view showing one embodiment of an apparatus of the present invention when used, respectively;

FIG. 3a is a perspective view of the apparatus of FIG. 1 showing the arrangement of the embedded retainers relative to each other and also showing the cut ends of the digestive tract just before they are placed into a groove in a support tube;

FIG. 3b is a longitudinal sectional view showing a portion of the tube dissolved away to reveal the retainers in a closed state clamping the cut ends of the digestive tract together;

FIGS. 11 and 12 are a longitudinal sectional view and a transverse sectional view showing an other embodiment of an apparatus of the present invention when used, respectively;

DETAILED DESCRIPTION OF PREFERRED EMBODIMENTS

Figure 3:
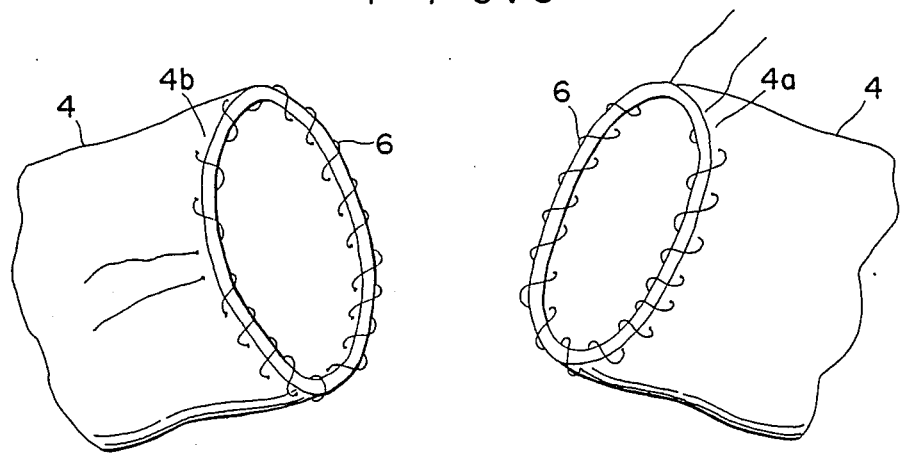
FIG. 3 is a perspective view showing the state of a digestive tract prior to use of the anastomosing apparatus.

Preferred embodiments of the apparatus of the present invention will be described below with reference to the drawings.

In FIGS. 1 and 2, designated at the reference numeral 1 is an anastomosing apparatus which is composed of a support tube 2 formed of mainly saccharides, e.q., disaccharides such as palatinose, as a soluble material, and a plurality of belt-like retainers 3 each formed of a shape memory alloy.

As an example of end-to-end anastomosis both cut ends 4a, 4b of a digestive tract 4 are severed and inserted over the opposite ends of the support tube 2 as shown in FIG. 3a. The support tube 2 has a cylindrical shape with an outer diameter of about 20-30 mm, an inner diameter of about 6 mm and a length of about 50 mm. A groove 5 is formed on the outer periphery in an annular shape with a width and a depth of approximately 4 mm. The belt-like retainers 3 each have an approximately 16 mm length and are shaped into a substantially U-form (channel-like form in the illustrated example). A total of 12 to 20 retainers 3 are arranged around the groove 5 of the support tube 2 in a radially arrayed pattern with the open space between the spaced apart ends of each retainer directed outward. Each retainer 3 is buried in the support tube 2 along both the inner side surfaces and the inner bottom surface of the groove 5 to a depth of approximately 1 mm.

Furthermore, the retainers 3 are buried in the support tube 2 in an open state, the spaced apart ends of the plurality of retainers defining a channel-like configuration which has a spacing between its open spaced apart ends wider than that of the memorized intrinsic closed state shape. The retainer 3 has such a property that it returns to the memorized intrinsic shape which has a spacing between its open spaced apart ends narrower than that in the configuration of FIG. 1, when the temperature of the retainer 3 is raised up to the body temperature of 36° to 40° C.

The apparatus 1 is used as follows. After excising the diseased portion of the digestive tract 4, both cut ends 4a, 4b of the digestive tract 4 are respectively tied up by running a stitch using a thread 6 such as a non-processed (plain) cat gut which will be absorbed in about a week, as shown in FIG. 3. Then, as shown in FIGS. 1 and 3a, opposite ends of the support tube 2 are inserted into the cut ends 4a, 4b, respectively, and the cut ends 4a, 4b are engaged with the groove 5 of the support tube 2 by tightening the thread 6 used for the above running stitch. In this state, the outer layers of both the cut ends 4a, 4b are sutured with a thread 7 using as many as 8-10 stitches for reinforcement.

Figure 4:
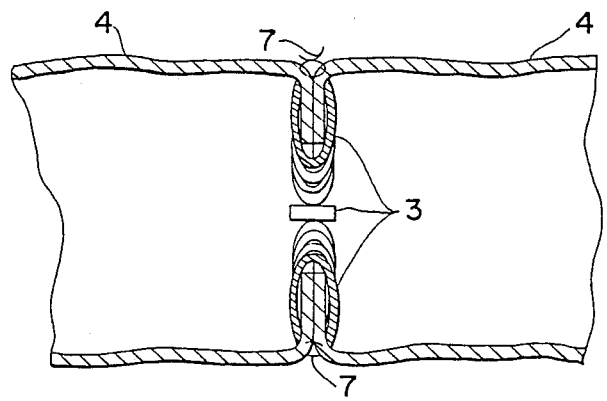
FIG. 4 is a longitudinal sectional view showing the state of the digestive tract after use of the anastomosing apparatus.

With the lapse of time in that state, the support tube 2 falls into pieces gradually as the saccharides composing the support tube 2 are dissolved as shown in FIG. 3b. After about 1 hour, a plurality of retainers 3 become separated from the support tube 2 as shown in FIG. 4. At the same time, since the temperature of the respective retainers 3 is raised by the body temperature, they are caused to return to their intrinsic shape as shown in FIG. 3b, thereby moving the spaced apart retainer ends to a closed state. Thus, the cut ends 4a, 4b of the anastomosed digestive tract 4 are pinched and held by the retainers 3 in the same manner as the albert's suture of the standard two-layer inversion anastomosis.

Then, as time goes by in the above state, the cut ends 4a, 4b of the digestive tract 4 adhere to each other outside the radially arranged retainers 3. After one or two weeks, when the parts of the anastomosed digestive tract 4 held by the retainers 3 inside the adhered portion are necrotized, the retainers 3 fall off inside the digestive tract 4 and are automatically excreted.

Figure 15:
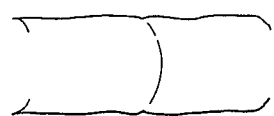
FIGS. 15 through 17 are explanatory views of an anastomosing portion.
Figure 16:
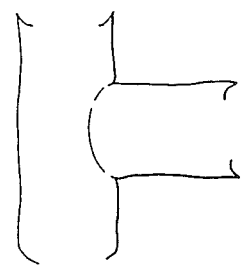
Figure 17:
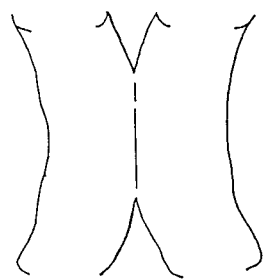

As described above, since a plurality of retainers 3 used in the apparatus 1 of the present invention separately fall off after completing their intended mission and are each sufficiently small in size, the respective retainers 3 are automatically excreted without the need of special attention, with the result that safety is improved and a burden imposed on patients is lessened. The apparatus 1 of the present invention can be applied to any of the foregoing embodiments, end-to-end anastomosis as shown in FIG. 15, end-to-side anastomosis as shown in FIG. 16, as well as side-to-side anastomosis as shown in FIG. 17.

Further, since a plurality of retainers 3 are arranged in a radial pattern, the cut ends 4a, 4b can be held in the same manner as the standard two-layer inversion anastomosis and, blood flow in the region of the cut ends 4a, 4b is secured. In addition, the retainers 3 are each caused to close their open spaced apart ends due to its property of memorizing the intrinsic closed shape, so it is not necessary to perform a closing operation by the use of a special closure appliance, such as staples, which have been used in the past. Accordingly, there is no fear that the appliance may traumatize the surrounding organs and tissues, and there is no need of repairing the hole through which the appliance has been inserted. As a result, the possibility of stenosis is small, the post-operation recuperation becomes more satisfactory, and earlier recovery can be expected.

Figure 5:
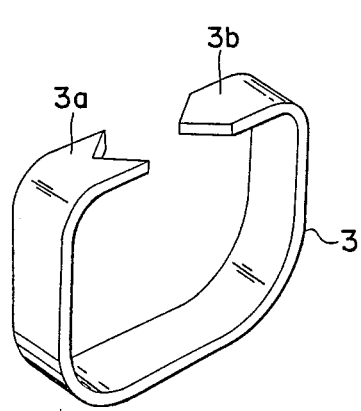
FIGS. 5 and 6 are perspective views showing modifications of a retainer.
Figure 6:
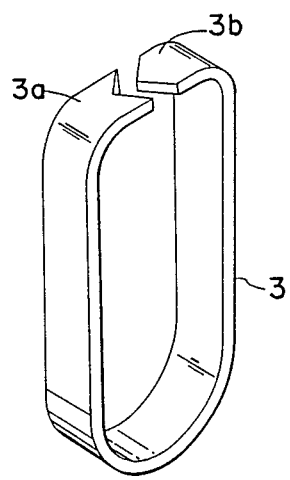
Figure 7:
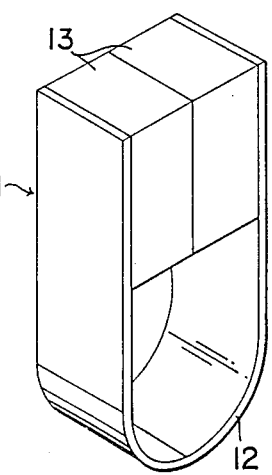
FIG. 7 is a perspective view showing another modification of the retainer.

The foregoing embodiment, for example, may be modified such that engagement portions 3a, 3b are respectively formed at the open opposite ends of the retainer 3 as shown in FIG. 5, and the engagement portions 3a, 3b are caused to engage with each other as shown in FIG. 6, when the retainer 3 closes the open opposite ends. In addition to a shape memory alloy, the retainer 3 may be formed of a shape memory resin which has a similar property as the shape memory alloy, or of a spring member. As alternative retainer 11 may be fabricated, as shown in FIG. 7, by attaching a pair of magnets 13 that will attract each other, to each of the spaced apart ends of a connecting plate 12 made of synthetic resin or the like.

While the support tube 2 is mainly formed of a soluble material such as saccharides, it is not always necessary for the support tube 2 to be entirely soluble. For example, it may be fabricated by solidifying particles of an insoluble material, which will not affect human bodies, with soluble material. In addition to saccharides, starch bound with excipient, glue, and soluble synthetic resin may be included in the soluble material.

Figure 8:
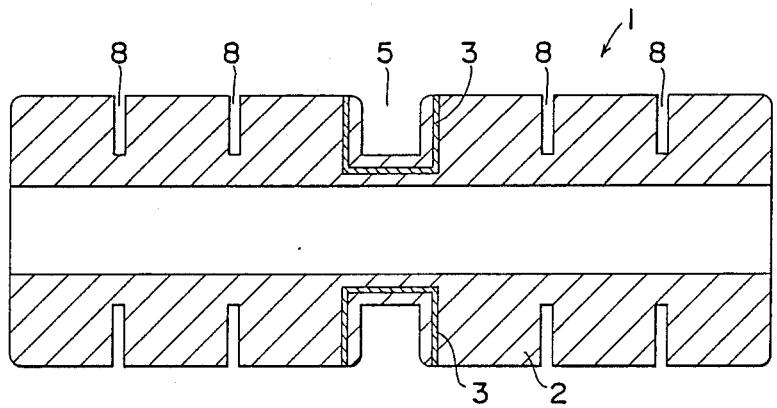
FIGS. 8 through 10 are sectional views each showing modified forms of a support tube.
Figure 9:
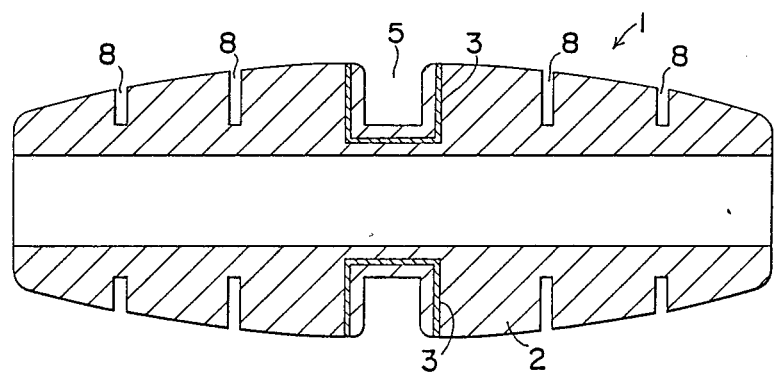
Figure 10:
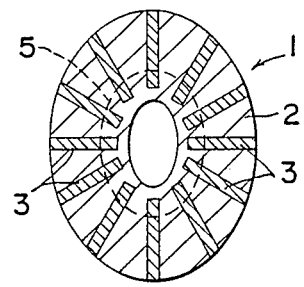

Furthermore, with annular cutouts 8 formed on the outer periphery of the support tube 2, as shown in FIGS. 8 and 9, the support tube 2 can be adjusted in its length by cutting it at any of the cutouts 8. This makes it possible to easily apply the apparatus 1 of the present invention to the end-to-side and side-to-side anastomoses as shown in FIGS. 16 and 17 too. As an alternative, when the support tube 2 is shaped to have an ellipsoidal cross section as shown in FIG. 10, it becomes optimum for use in the side-to-side anastomosis as shown in FIG. 17. Though not shown, when the support tube 2 is bent to a substantially V-shape, it is suitable for use in the bent V-shape.

Figure 13:
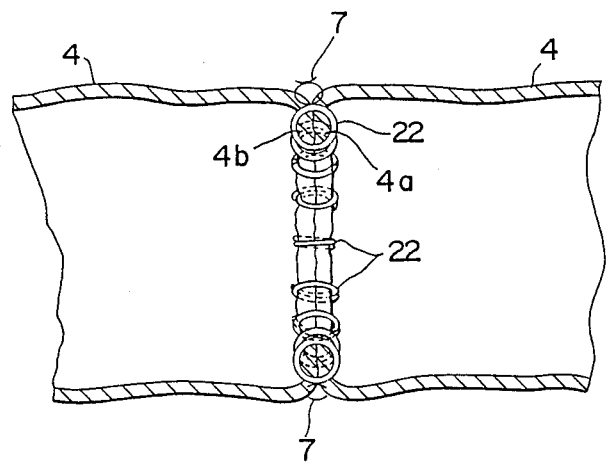
FIG. 13 is a longitudinal sectional view showing the state of the digestive tract after use.

FIGS. 11 through 13 show an anastomosing apparatus 21 of an another embodiment of the present invention. This embodiment is similar to the foregoing embodiment except as to the retainer shape. Accordingly, in the explanation of an anastomosing apparatus 21 of this embodiment, the same components as those of the anastomosing apparatus 1 in the foregoing embodiment are designated by the same reference nemerals and the detailed explanations thereof are omitted.

The retainer 22 in this embodiment is made of a shape memory alloy of a wire shape with length of about 13.3 mm and outer diameter of about 0.3 mm and returns to the memorized intrinsic shape when the temperature of the retainer 22 is raised up to about (30±5)°C. The groove 5 of the support tube 2 has width of about 4 mm and depth of about 4 mm. The memorized intrinsic shape of the retainer 22 is a circle or coil shape with diameter of about 2 or 3 mm, rounded about 2.1~1.4 times, and at least both ends of which are overlapped. As shown in FIGS. 11 and 12, a total of 15 to 24 retainers 22 are arranged around the groove 5 in the support tube 2 in a radial pattern with a circumferential spacing of about 4 mm, respectively, on the outer-periphery of the support tube 2 having outer diameter of about 20 to 30 mm. Each retainer 22 is buried in the support tube 2 along both the inner side surfaces and the inner bottom surface of the groove 5. Further, in the support tube 2 each retainer 22 is forcibly opened so that the plurality of retainers define a channel-like configuration circumscribing the square groove 5 of the support tube 2 having width and depth of about 4 mm with the open space between each of the spaced apart retainer ends directed outward.

The apparatus 21 is used similar to the apparatus 1 mentioned already. After both cut ends 4a, 4b of the digestive tract 4 are processed as explained with reference to FIG. 3, the cut ends 4a, 4b of the digestive tract 4 are engaged with the groove 5 of the support tube 2 as shown in FIG. 11 and as explained with reference to FIG. 1.

With the lapse of time in that state, the support tube 2 is dissolved. At the same time, since the temperature of the respective retainers 22 is raised by the body temperature, they are caused to return to their intrinsic coil shape as shown in FIG. 13, so that the open opposite ends are penetrated into the cut ends 4a, 4b and closed. Thus, the cut ends 4a, 4b of the anastomosed digestive tract 4 are squeezed and held by the retainers 22 in the same manner as the albert's suture of the standard two-layer inversion anastomosis.

In this case, the cut ends 4a, 4b of the digestive tract 4 are squeezed together because the cross-sectional area of the cut ends 4a, 4b of the digestive tract 4 squeezed by the retainers 22 are larger than the area of the retainer circle which has a diameter of about 2 to 3 mm, which is the intrinsic shape of the retainer 22.

Specifically, if the running stitch by a thread 6 is formed on the digestive tract 4 at a portion spaced away 2 mm from the cut ends 4a, 4b thereof, it is considered that the distance of 2 mm is reduced to one half, i.e., 1 mm when the thread 6 used for the running stitching is tightened to engage the cut ends 4a, 4b with the groove 5. If so, portions of the cut ends 4a, 4b of about 5 mm in length are inserted into the groove 5 which is about 4 mm in depth. The cross-sectional area of the cut ends 4a, 4b inserted into the groove 5, that is, the cross-sectional area of the cut ends 4a, 4b squeezed by the retainers 22 becomes 15 mm² in the case where the digestive tract 4 in the normal state is 1.5 mm in thickness, and becomes 20 mm² in the case where the digestive tract 4 in the normal state is 2 mm in thickness, whereas the area of the circle of about 2 to 3 mm in diameter which is the intrinsic shape of the retainer 22 is too small as 3.14~7.065 mm², so that the cut ends 4a, 4b of the digestive tract 4 is squeezed under the shrinking state by the retainers 22.

Then, as time goes by in the above state, the cut ends 4a, 4b of the digestive tract 4 adhere to each other outside the radially arranged retainers 22 in the same manner as when the apparatus 1 is used. When the parts of the anastomosed digestive tract 4 held by the retainers 22 inside the adhered portion are necrotized, the retainers 22 fall off inside the digestive tract 4 and then automatically excreted, so that a function and effect similar to that explained in the case of apparatus 1 can be obtained.

In addition to a shape memory alloy, the retainer 22 may be formed of a shape memory resin which has a similar property as the shape memory alloy or a spring member.

The retainer 22 can be mass produced easily by manufacturing a lengthy coil rounded many times and cutting it into several coil peaces rounded a predetermined times.

Figure 14:
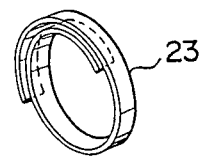
FIG. 14 is a perspective view showing other modification of the retainer.

Further, in this embodiment, the retainer 22 of wire shape is used. However, a belt-like helical retainer 23 as shown in FIG. 14 may used instead of said retainer 22.

As described above, according to the apparatus of the present invention, since a plurality of retainers separately fall off inside a digestive tract after attaining their intended purpose and are each sufficiently small in size, the respective retainers are automatically excreted without the need of special attention, with the result that safety is improved, a burden imposed on patients is lessened, and the possibility of stenosis is reduced.

Where saccharides are used as the soluble material of the support tube, human bodies are less affected. Where the retainers are each formed in a circle, the retainers become suitable for mass production. Further, where the retainers are each made of a shape memory alloy or resin, the force of closing the spaced apart ends of each retainer can be sustained until the time of use, even when a storage period prior to use is prolonged. The retainers can easily buried into the support tube. Where the retainers use spring members, they can be manufactured less expensively. Where the retainers are each provided at their spaced apart ends with magnets attracting each other, the held portions of the cut ends of the digestive tract are brought into surface-to-surface pressure contact.

What is claimed is:

1. An apparatus for anastomosing a digestive tract comprising: a support tube formed mainly of a soluble material and having an outer periphery; an annular groove in said outer periphery having spaced apart inner sides and an inner bottom surface; and a plurality of individual retainers each having spaced apart ends providing an open space therebetween when said retainer is in an open state, said retainer endowed with a property of moving said spaced apart ends to a closed state during use wherein said digestive tract is clamped therebetween, said retainers disposed in said support tube in said open state around said inner side and bottom surfaces at a plurality of spaced apart locations along said groove, said retainers being released from said support tube and allowed to assume said closed state as the soluble material of said support tube is dissolved.

2. The apparatus for anastomosing a digestive tract according to claim 1 wherein said support tube is made of saccharides.

3. The apparatus for anastomosing a digestive tract according to claim 1 wherein said spaced apart ends of the retainer are opposite to each other when they are moved to said closed state.

4. The apparatus for anastomosing a digestive tract according to claim 1 wherein said retainer is substantially U-shaped and is embedded in the support tube along both the inner side surfaces and the inner bottom surface of the groove with the inner bottom surface of the groove with said spaced apart ends in said open state.

5. The apparatus for anastomosing a digestive tract according to claim 1 wherein said spaced apart ends of the retainer overlap each other when said retainer is in said closed state.

6. The apparatus for anastomosing a digestive tract according to claim 1 wherein said retainer is in a substantially arcuate shape when in said open state and is embedded in said support tube along both the inner side surfaces and the inner bottom surface of said annular groove, said retainer forming a circle when said spaced apart ends move to said closed state.

7. The apparatus for anastomosing a digestive tract according to claim 1 wherein said retainer is made of an alloy having a memory enabling said retainer to return to a memorized intrinsic closed state at a predetermined temperature so that after said tube is installed said spaced apart ends will move to said closed state at said predetermined temperature.

8. The apparatus for anastomosing a digestive tract according to claim 1 wherein said retainer is made of resin having a property of closing said spaced apart ends when said retainer is at a predetermined temperature.

9. The apparatus for anastomosing a digestive tract according to claim 1 wherein said retainer is a spring member.

10. The apparatus for anastomosing a digestive tract according to claim 1 wherein each of said spaced apart ends of said retainer has a magnet, with the magnet on one of said spaced apart ends being attracted to the magnet on the other of said spaced apart ends opposite thereto.

* * * * *